(12) United States Patent
Gregor et al.

(10) Patent No.: US 8,697,449 B2
(45) Date of Patent: Apr. 15, 2014

(54) OPTICAL BLOOD COAGULATION MONITOR AND METHOD

(75) Inventors: Brian Gregor, Sudbury, MA (US); Rama Bansil, Dover, MA (US); Julian D. Spring, Allston, MA (US)

(73) Assignee: Spectral Sciences, Inc., Burlington, MA (US)

(*) Notice: Subject to any disclaimer, the term of this patent is extended or adjusted under 35 U.S.C. 154(b) by 0 days.

(21) Appl. No.: 13/435,052

(22) Filed: Mar. 30, 2012

(65) Prior Publication Data
US 2012/0252127 A1 Oct. 4, 2012

Related U.S. Application Data

(60) Provisional application No. 61/470,610, filed on Apr. 1, 2011.

(51) Int. Cl.
| | |
|---|---|
| *G01N 33/86* | (2006.01) |
| *G01N 33/48* | (2006.01) |
| *G01N 21/47* | (2006.01) |
| *G01N 21/49* | (2006.01) |
| *G01N 21/51* | (2006.01) |

(52) U.S. Cl.
USPC ............... 436/69; 436/63; 436/164; 422/73; 422/82.05; 422/82.09; 73/64.41; 73/64.43; 600/369; 356/39

(58) Field of Classification Search
USPC ............ 436/63, 69, 164, 165; 422/68.1, 73, 422/82.05, 82.09; 435/13, 29; 73/64.41, 73/64.43; 600/369; 356/39
See application file for complete search history.

(56) References Cited

U.S. PATENT DOCUMENTS

| | | | | |
|---|---|---|---|---|
| 3,450,501 A | * | 6/1969 | Oberhardt | 422/73 |
| 3,695,842 A | | 10/1972 | Mintz | |
| 3,713,743 A | * | 1/1973 | Simms | 356/338 |
| 4,252,536 A | * | 2/1981 | Kishimoto et al. | 356/36 |
| 4,263,508 A | * | 4/1981 | Leary et al. | 250/358.1 |
| 4,766,083 A | * | 8/1988 | Miyashita et al. | 436/517 |
| 4,777,141 A | | 10/1988 | Calzi et al. | |
| 5,526,111 A | | 6/1996 | Collins et al. | |
| 6,255,126 B1 | | 7/2001 | Mathieu et al. | |
| 7,126,676 B2 | * | 10/2006 | Greco | 356/39 |
| 7,276,376 B2 | * | 10/2007 | Katayama et al. | 436/69 |
| 7,821,620 B2 | * | 10/2010 | Dogariu | 356/39 |
| 2009/0209834 A1 | * | 8/2009 | Fine | 600/316 |
| 2010/0248278 A1 | * | 9/2010 | Pouteau et al. | 435/13 |

OTHER PUBLICATIONS

Piederriere et al. Journal of Biomedical Optics, vol. 9, No. 2, Mar./Apr. 2004, pp. 408-412.*

(Continued)

*Primary Examiner* — Maureen Wallenhorst
(74) *Attorney, Agent, or Firm* — Brian M. Dingman; Dingman IP Law, PC

(57) ABSTRACT

An optical blood coagulation monitor and method. The monitor has a blood sample holder, a laser with its output light directed through the blood sample, a two-dimensional detector that is able to detect light at the laser light wavelength and that has a detector output, optics for imaging onto the detector laser light that is forward scattered by the blood, and a data analysis system, responsive to the detector output, that is adapted to analyze the detected light to provide information on time-resolved coagulation and clotting properties of the blood.

17 Claims, 4 Drawing Sheets

(56) References Cited

OTHER PUBLICATIONS

Amin, M.S., Park, Y., Lue, N., Dasari, R.R, Badizadegen, K., Feld, M.S., Popescu, G. "Microrheology of red blood cell membranes using dynamic scattering microscopy." Optics Express 15.25 (2007): 17001-9. PMID: 19550991.

Bansil, R., Lal, J., Carvalho, B. "Effects of gelation on spinodal decomposition kinetics in gelatin." Polymer 33.14 (1992): 2961-9, Abstract.

Bansil, R., Liao, G., Falus, P. "Kinetics of spinodal decomposition in chemically crosslinked gels." Physical A 231.1-3 (1996): 346-58, Abstract.

Brohi, K., Singh, J., Heron, M., Coats, T. "Acute traumatic coagulopathy." J Trauma 54.6 (2003): 1127-30. PMID: 12813333, Abstract.

Burghardt, W.R., Goldstick, T.K., Leneschmidt, J., Kempka, K. "Nonlinear viscoelasticity and thromboelastography: 1. Studies on bovine plasma clots." Biorheology 32.6 (1995): 621-30. PMID: 8857352.

Cosgriff, N., Moore, E.E., Sauaia, A., Kenny-Moynihan, M., Burch, J.M., Galloway, B. "Predicting life-threatening coagulopathy in the massively transfused trauma patient: hypothermia and acidoses revisited." J Trauma 42.5 (1997): 857-61. PMID: 9191667.

Ferri F, Greco M, Arcòvito G, De Spirito M, Rocco M."Structure of fibrin gels studied by elastic light scattering techniques: dependence of fractal dimension, gel crossover length, fiber diameter, and fiber density on monomer concentration." Phys Rev E 66, 11913, 2002.

Kita, R., Takahashi, A., Kaibara, M., Kubota, K. "Formation of fibrin gel in fibrinogen-thrombin system: static and dynamic light scattering study." Biomacromolecules, 3, 5 (2002): 1013-20. PMID: 12217048, Abstract.

MacLeod, J.B., Lynn, M., McKenney, M.G., Cohn, S.M., Murtha, M. "Early coagulopathy predicts mortality in trauma." J Trauma 55.1 (2003): 39-44. PMID: 12855879.

Mie, G. "Beiträge zur Optik trüuber Medien, speziell kolloidaler Metallösungen." Ann. Phys. 330.3 (1908): 377-445.

Mohandas, N., Kim, Y.R., Tycko, D.H., Orlik, J., Wyatt, J., Groner, W. "Accurate and independent measurement of volume and hemoglobin concentration of individual red cells by laser light scattering." Blood 68.2 (1986): 506-13. PMID: 3730613.

Nystrup, K., Windeløv, N., Thomsen, A., and Johansson, P. "Reduced cot strength upon admission, evaluated by thrombelastography (TEG), in trauma patients is independently associated with increased 30-day mortality." Scandinavian Journal of Trauma, Resuscitation and Emergency Medicine 2011 19:52.

Park, Y., Best-Popescu, C.A., Dasari, R.R., Popescu, G. "Light scattering of human red blood cells during metabolic remodeling of the membrane." J Biomed Opt. 16.1 (2011):011013. PMID: 21280900.

Park, Y., Diez-Silva, M., Fu, D., Popescu, G., Choi, W., Barman, I., Suresh, S., Feld, M.S. "Static and dynamic light scattering of healthy and malaria-parasite invaded red blood cells." J Biomed Opt. 15.2 (2010):020506. PMID: 20459219.

Sauaia, A.S., Moore, F.A., Moore, E.E., Moser, K.S., Brennan, R., Read, R.A, Pons, P.T. "Epidemiology of trauma deaths: a reassessment." J Trauma 38.2 (1995):185-93. PMID: 7869433, Abstract.

Viasnoff, V., Lequeux, F., and Pine, D.J. "Multispeckle diffusing-wave spectroscopy: A tool to study slow relaxation and time-dependent dynamics." Rev. Sci. Instrum. 73, 2336 (2002).

Zink, K.A., Sambasivan, C.N., Holcomb, J.B., Chisholm, G., Schreiber, M.A. "A high ratio of plasma and platelets to packed red blood cells in the first 6 hours of massive transfusion improves outcomes in a large multicenter study." Am J Surg 197.5 (2009): 565-70. PMID: 19393349, Abstract.

Borgman, M.A., Spinella, P.C., Perkins, J.G. Grathwohl, K.W., Repine, T. Beekley, A.C. Sebesta, J., Jenkins, D., Wade, C.E., Holcomb, J.B. "The ratio of blood products transfused affects mortality in patienst receiving massive transfusions at a combat support hospital." J. Trauma 63.4 (2007): 805-13. PMID: 18090009.

Evans, P.A., Hawkins, K., Williams, P.R., Wiliams, R.L. "Rheometrical detection of incipient blood clot formation by Fourier transform mechanical spectroscopy." J Non-Newtonian Fluid Mech 148. 1-3 (2008): 122-6, Abstract.

\* cited by examiner

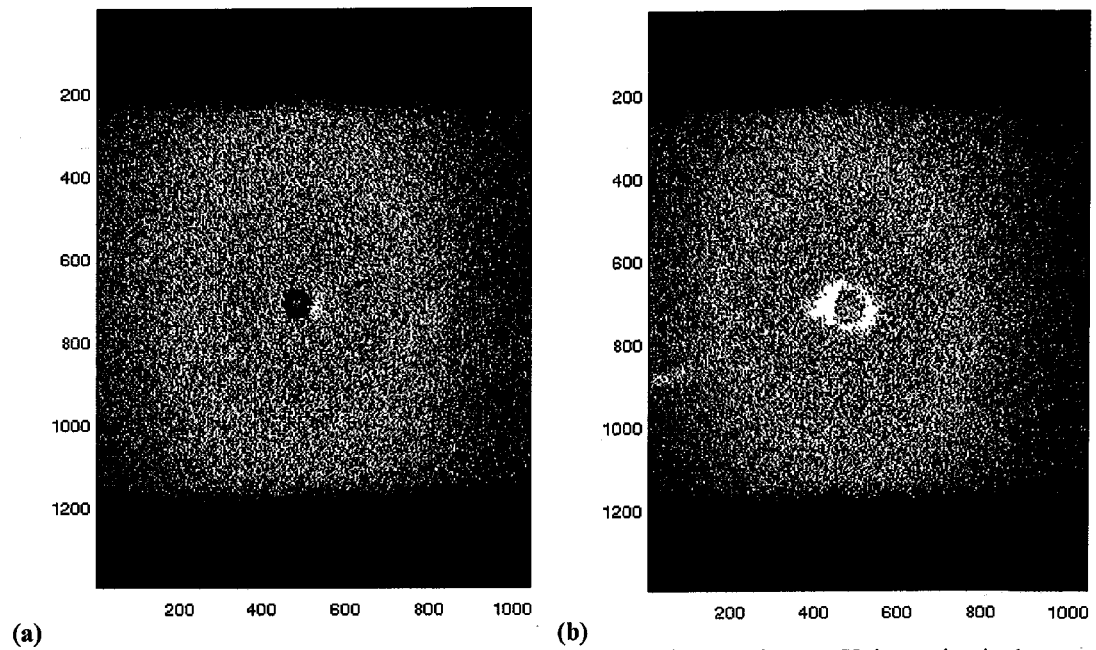
Figure 2. Citrated swine blood at 37C (a) at time 0, (b) after 30 minutes. Units are in pixels
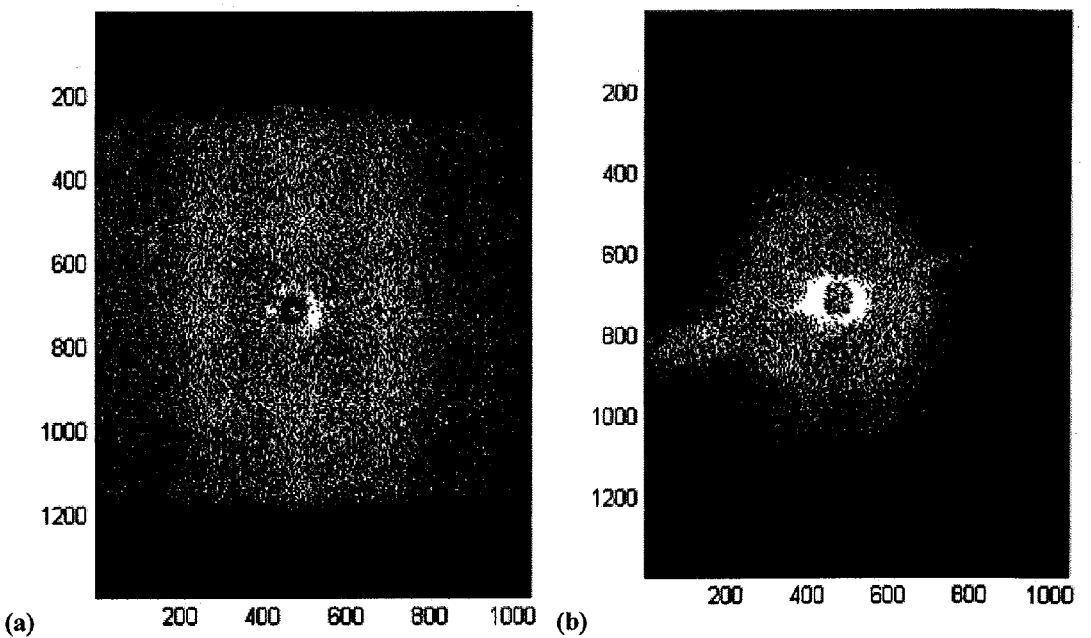
Figure 3. (a) Recalcified blood at 37C uncoagulated at the start of the data collection, (b) coagulation proceeding after 30 minutes. The diagonal line is an instrument effect, most likely due to stray light reflections. Units are in pixels.

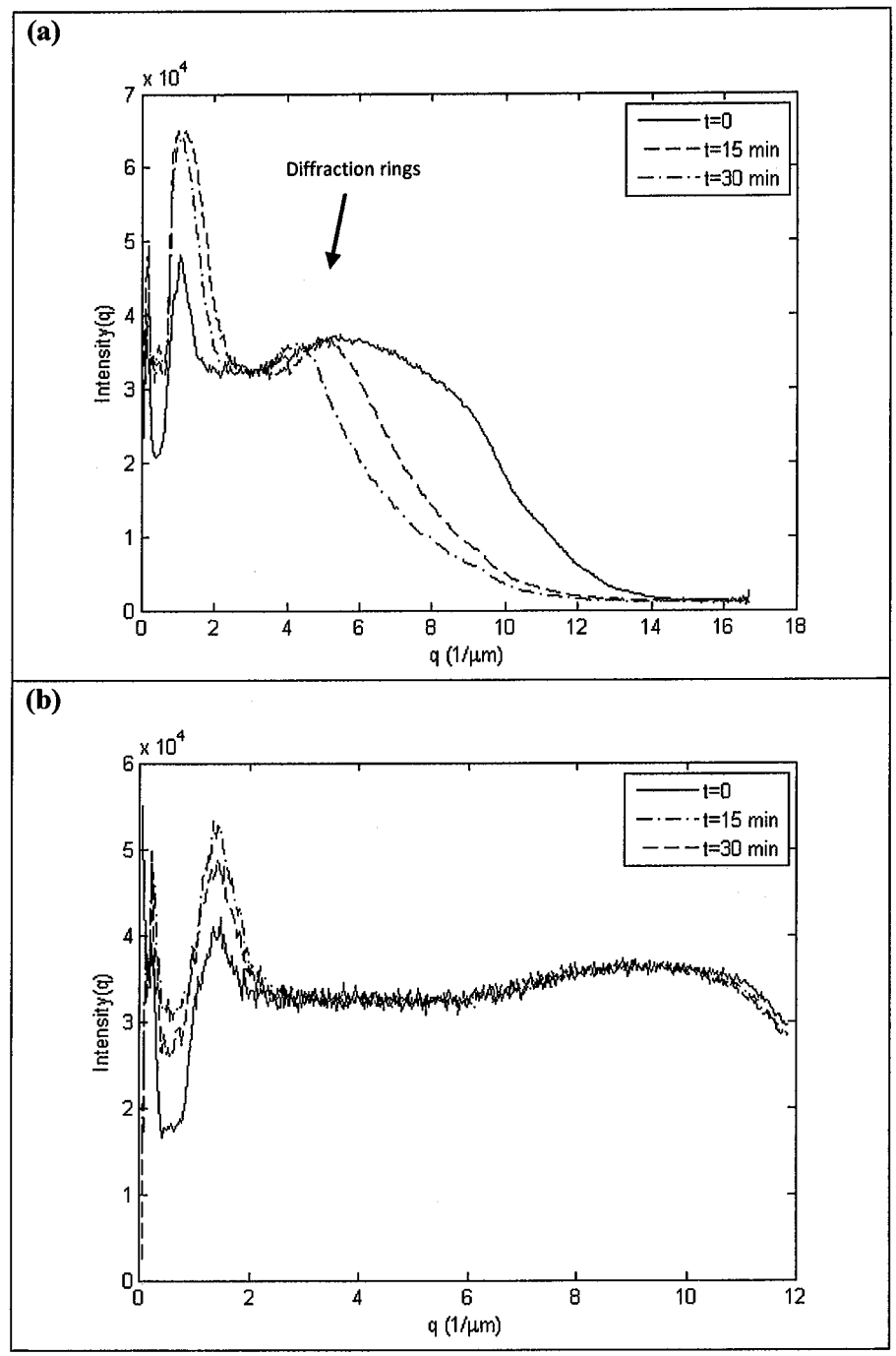
Figure 4. Azimuthal averages of CCD images

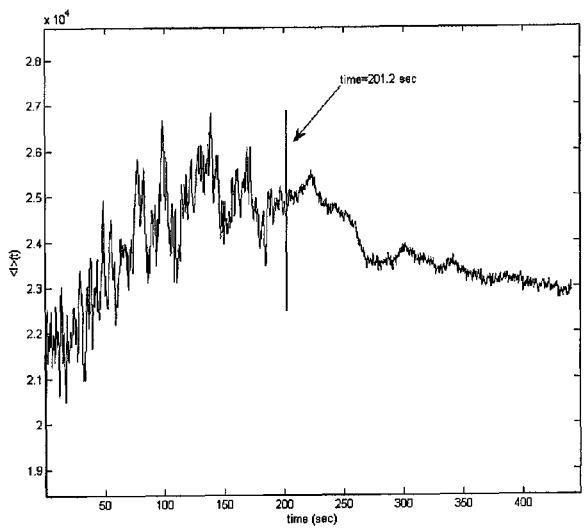
Figure 5. Change over time in averaged intensity over a 50x50 pixel box for blood with kaolin added.
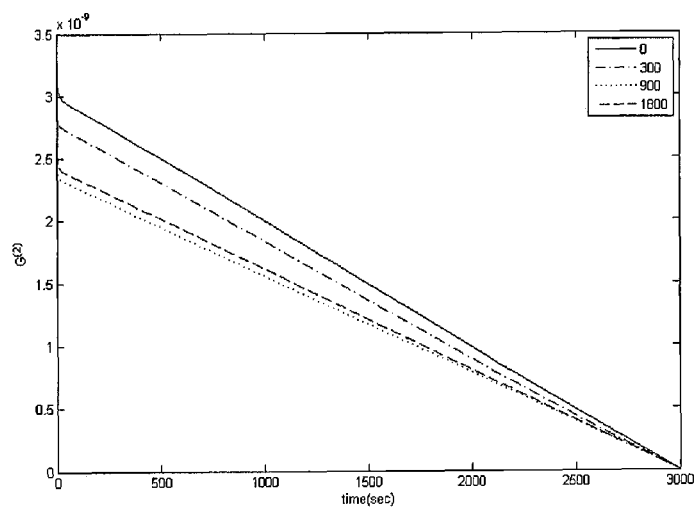
Figure 6. Auto correlation curves at 0 (solid), 300 (dash-dot), 900 (dot), and 1800 (dash) seconds during coagulation of a recalcified swine blood sample

OPTICAL BLOOD COAGULATION MONITOR AND METHOD

CROSS-REFERENCE TO RELATED APPLICATION

This application claims priority of Provisional Application Ser. No. 61/470,610 filed on Apr. 1, 2011, the disclosure of which is incorporated herein by reference.

FIELD

This disclosure relates to an optical device used to study the coagulation and clotting properties of blood.

BACKGROUND

Blood loss in patients with severe trauma can be significantly worsened by coagulopathy, a condition in which blood fails to clot appropriately. Hemorrhage is the cause of 40% of trauma deaths worldwide. Acidosis, hypothermia, and coagulopathy constitute a "bloody vicious cycle" of massive trauma, hemorrhage, resuscitation, hemodilution, coagulopathy and continued bleeding. The coagulopathy of trauma is a deficiency in the body's mechanism for blood clotting, observed as bleeding from non-injured sites such as intravenous lines and tissue oozing after surgical management of identifiable vascular bleeding. Over the past several years studies have pointed to the coagulopathy of trauma as an early event that is identifiable at the time of presentation, and more importantly, that early coagulopathy predicts higher mortality. This has led to efforts to identify patients at high risk of coagulopathy and to pre-empt it by such strategies as early plasma transfusion, in both military and civilian trauma.

Instruments to study and measure the coagulation and clotting properties of blood include technologies based on measuring shear forces, chemical reactions, and optical transmission. The thromboelastograph (TEG) [U.S. Pat. No. 6,225,126] is a device that measures the shear forces on a pin suspended in a droplet of blood sitting in a cup via a wire. As the cup is rotated back and forth through a small angular displacement the clot formation causes torsion on the wire, which is measured by the instrument. The TEG directly measures the change in viscoelastic behavior as the clot is formed. This instrument is a standard device used in the diagnosis of coagulopathy. The volume of blood used by the TEG is large enough to require sampling from a patient's veins and the instrument is very vibration sensitive. An alternative device performs a chemical measurement to determine the response of a blood sample to the drug warfarin [U.S. Pat. No. 5,526,111]. Another instrument on the market is an optical turbidity monitor that uses a simple photodetector and light source. The photodetector based instrument monitors the transmission of an incoherent light source through a blood sample, and when the transmitted light reaches a predetermined threshold correlated with clot formation the elapsed time is recorded [U.S. Pat. No. 4,777,141]. Another instrument uses the displacement of ferrite beads [U.S. Pat. No. 3,695,842]. The instrument detects magnetic flux through a ferrite bead immersed in a blood droplet. The displacement of the bead during coagulation is measured through changes in the magnetic flux.

SUMMARY

The disclosure herein involves study of the dynamic behavior of a blood droplet while it undergoes coagulation and clot formation by measuring scattered light from a laser source using one or more two-dimensional detectors, including but not limited to a charge coupled device (CCD) or complementary metal oxide semiconductor (CMOS) detector arrays. Laser light passing through a blood droplet contained in a hemocompatible sample holder is scattered by the various blood components. Light scattering has been used to study several properties of blood and its components. In this innovation several types of scattered light measurements are used to determine physical parameters of the coagulating blood sample. The sample stage is optionally temperature controlled so that the instrument can be used in a wider array of environmental conditions or to simulate physiological conditions. The scattered light is imaged onto the detector array and the images are recorded over a period of time. The various blood components cause diffraction patterns in the scattered light which correspond to the state of coagulation and clot formation in the blood droplet in a time resolved manner. The sample droplet can be any type of blood (e.g. fresh whole blood, recalcified, citrated, etc.) or blood plasma. The sample can optionally contain coagulation activators, or coagulation inhibitors, or additives such as microspheres to enhance scattering. The sample holder itself is optically transparent at the wavelength of the laser and will not support clot formation on its surface through the use of appropriate hydrophobic or anti-coagulant materials or coatings. The result of the measurement is a set of parameters that provide detailed information on the time resolved coagulation and clotting properties of the sample droplet. The device is capable of several simultaneous measurements, including the absorption coefficient of the sample droplet, time-resolved static light scattering, and time-resolved dynamic light scattering. These measurements provide information on the time the blood droplet takes to form a fibrin gel network (i.e., the point at which a clot begins), the dynamics of a characteristic size of the clot over time, the dynamics of fibrinolysis, and a dynamic measure of the strength of the clot.

This disclosure features a method of determining properties of blood comprising providing a blood sample, providing a laser and directing light from the laser through the blood sample, detecting over a period of time laser light that is forward scattered by the blood, and analyzing the detected light to provide information on time-resolved coagulation and clotting properties of the blood. The provided information may comprise the time for a clot to start forming, the rate of clot formation, and the strength of the clot. The wavelength of the laser may be in the visible to near infrared range. The detecting step may comprise recording the position of the first order diffraction ring.

The analyzing step may comprise determining a time dependent statistical behavior of detected laser speckle intensities. The method may further comprise adding hemocompatible microspheres to the blood sample before directing laser light through the sample. The method may further comprise detecting the intensity of unscattered laser light that has passed through the blood sample. The analyzing step may comprise determining the turbidity of the blood based on the detected unscattered laser light. The detecting step may comprise sampling a single laser speckle or a plurality of speckles over time. The analyzing step may comprise calculating an autocorrelation curve for each sampled speckle, and averaging the set of autocorrelations.

Also featured is an optical blood coagulation monitor comprising a blood sample holder, a laser with its output light directed through the blood sample, a two-dimensional detector that is able to detect light at the laser light wavelength and that has a detector output, optics for imaging onto the detector laser light that is forward scattered by the blood, and a data analysis system, responsive to the detector output, that is adapted to analyze the detected light to provide information on time-resolved coagulation and clotting properties of the blood.

The provided information may comprise the time for a clot to start forming, the rate of clot formation, and the strength of the clot. The wavelength of the laser may be in the visible to near infrared range. The data analysis system may record the position of the first order diffraction ring. The data analysis system may determine a time dependent behavior of detected laser speckle patterns. The optical blood coagulation monitor may further comprise hemocompatible microspheres that are added to the blood sample before directing laser light through the sample.

The optical blood coagulation monitor may further comprise a detector for detecting the intensity of unscattered laser light that has passed through the blood sample. The data analysis system may determine the turbidity of the blood based on the detected unscattered laser light. The data analysis system may sample a single laser speckle or a plurality of speckles over time. The data analysis system may calculate an autocorrelation curve for each sampled speckle, and averages the set of autocorrelations.

Further featured herein is an optical blood coagulation monitor comprising a blood sample holder, a laser with its output light directed through the blood sample, wherein the wavelength of the laser is in the visible to near infrared range, a two-dimensional detector that is able to detect light at the laser light wavelength and that has a detector output, optics for imaging onto the detector laser light that is forward scattered by the blood, and a data analysis system, responsive to the detector output, that is adapted to analyze the detected light to provide information on time-resolved coagulation and clotting properties of the blood, wherein the provided information comprises the time for a clot to start forming, the rate of clot formation, and the strength of the clot. The data analysis system samples a single laser speckle or a plurality of speckles over time, and determines the time dependent behavior of the time-based detected laser intensity via the analysis methods of photon correlation spectroscopy.

BRIEF DESCRIPTION OF THE DRAWINGS

FIGS. 2a and 2b are scattered images from the monitor of FIG. 1 taken of citrated swine blood that did not coagulate.

FIGS. 3a and 3b are scattered images from the monitor of FIG. 1 taken of recalcified swine blood that did coagulate.

FIGS. 4a and 4b illustrate the magnitude of the wave vector with time for recalcified swine blood and citrated swine blood, respectively.

FIG. 5 illustrates average intensity over time for a blood sample that clotted.

FIG. 6 illustrate time-dependent behavior of auto calibration curves during coagulation of recalcified swine blood.

DETAILED DESCRIPTION OF EMBODIMENTS

Figure 1:
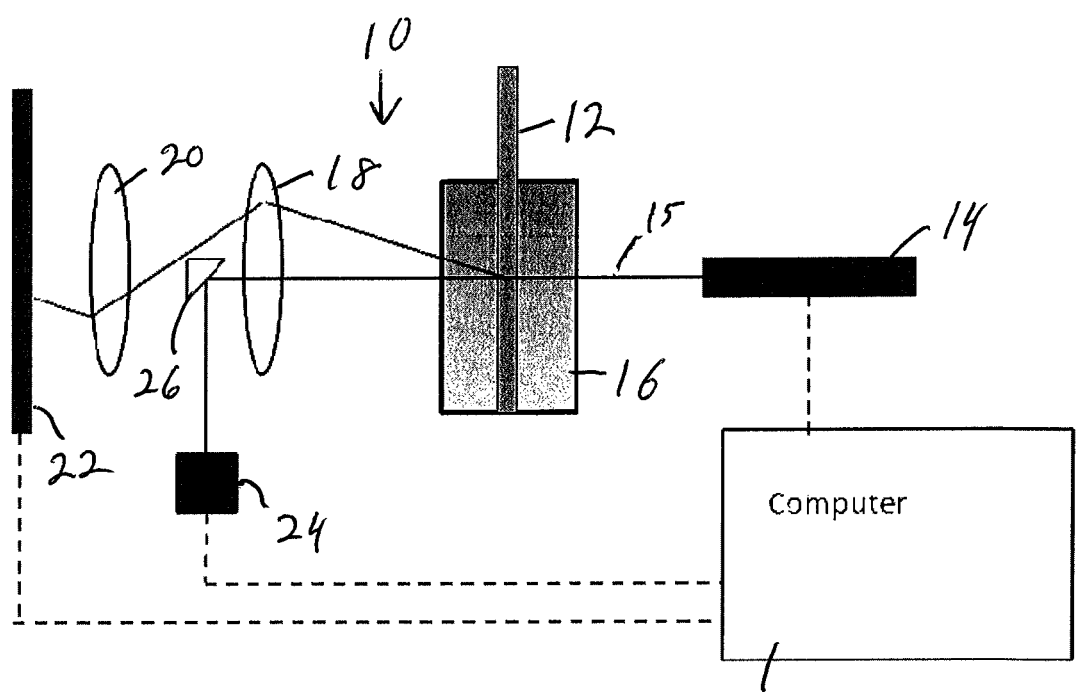
FIG. 1 is a schematic diagram of an optical blood coagulation monitor.

FIG. 1 shows a general representation of an optical blood coagulation monitor. Monitor 10 includes a laser source 14, a forward scattering detector array 22, and an optional additional photodetector 24 to which laser light is directed by mirror 26; photodetector 24 can be used to monitor the laser intensity over time. An optional second detector array to image larger scattering angles (described below) is not shown. The choice of laser wavelength and type of laser source may vary with the type of measurement desired. The laser light is collimated using standard techniques such as, but not limited to, the use of fiber coupling and a collimation lens or, alternatively, focusing the laser through a spatial filter and then re-collimating the beam with a lens, or the use of an anamorphic prism pair. There are several ways to image the scattered light from the sample. One approach is to use a set of reimaging lenses to project an image of scattered light onto the detector array. An alternative arrangement is to place a translucent screen next to the sample holder and then image the scattered light pattern from the screen onto the detector array using a set of lenses. Another alternative is to use a bundle of optical fibers collecting scattered light which are connected to portions of the detector array. Another alternative is to use imaging optics that image the scattered light onto a portion of the detector array and the laser speckle pattern onto another portion. Other alternatives would be apparent to those skilled in the technical field. Shown in FIG. 1 is lens 18 that images the scattering plane, and imaging lens 20.

The optical blood coagulation monitor/device improves upon the commercially available instruments for determining the ability of a patient's blood to coagulate. The measurement of wire torsion with the TEG leads to the determination of several parameters: when did coagulation begin, how fast did it proceed, what was the strongest clot state reached, and how strong is the final clot state. These parameters are combined in a heuristic fashion to create a coagulation index. The parameters measured with the TEG are the most similar to those measured by the disclosed device and the coagulation index is a standard characterization of coagulopathy. The sensitivity of the TEG is limited by the material properties of the wire and the sensitivity of the detection electronics and the interference in the coagulation process by the induced shear forces in the sample.

The device and method herein measures the time for a clot to start forming, the rate of clot formation, and the strength of the clot using a very different approach compared with the TEG. The preferred instrument 10 is diagrammed in FIG. 1. A collimated laser beam 15 passes through a thin blood sample. The blood sample must be thin enough so that the vast majority (typically >90%) of the scattered photons are scattered only a single time. The sample holder 12 is oriented orthogonally to the laser output and the sample stage 16 is optionally temperature controlled. A two dimensional detector array 22 with a pair of imaging lenses 18 and 20, positioned to capture light in the forward (<90 degree) angles, is used to image the scattered light. The amount of light falling on the detector array can be limited with any of several standard approaches, including but not limited to a variable or fixed size aperture, a polarizer, or a liquid crystal array. The images from the detector are provided to computer 30 over a time period, and corrected for detector noise and background light and can be analyzed in real-time or can be saved to computer storage for postprocessing.

The laser wavelength used in the data presented here was 808 nm, although the instrument and technique is not limited to that wavelength as any wavelength in the visible to near-infrared range could conceivably be used. It is advantageous for the laser wavelength to be selected to coincide with low optical absorption of hemoglobin, the primary absorbing component of blood, in order to avoid localized heating of the sample. The region from approximately 620 nm to 850 nm is the ideal wavelength range. Since scattering intensity decreases as the inverse fourth power of the wavelength the signal is decreased as the wavelength is increased. Longer infrared wavelengths results in significantly less information about the sample being collected as Rayleigh scatter dominates the signal.

The scattering angle can be calibrated in a number of ways and this disclosure is not limited to this specific calibration method. A dilute sample of 3 micron diameter latex microspheres in a buffer solution was used to calibrate the scattering angle. The microspheres produced a diffraction ring in the detector image which was analyzed using Mie theory to determine the scattering angle of the first diffraction ring based on the known size distribution of the microspheres. The location of the diffraction ring in the image and its angle and the cylindrical symmetry allows for the angular calibration of the image on the detector array in units of radians/pixel where the pixel distance is measured from the center of the laser.

When a blood sample is placed into the instrument the laser is scattered by the various blood components, producing a diffraction ring pattern that is the result of the collective scattering. The detector then records the changes in the diffraction pattern over time. FIG. 2 shows images from citrated swine blood at 37° C. over a 30 minute time period (FIG. 2a at 0 minutes and FIG. 2b at 30 minutes) wherein the blood does not coagulate. FIG. 3 shows images of scattered light from whole swine blood at 37° C. which coagulates over 30 minutes (FIG. 3a at 0 minutes and FIG. 3b at 30 minutes; units in pixels). The diagonal line in FIG. 3b is an instrument effect, most likely due to stray light reflections. These images are of the blocked direct beam at the center of the image and the first diffraction ring. There are several aspects to the recorded signal that are part of the data analysis. The first is the position of the $1^{St}$ order diffraction ring with time as the blood droplet coagulates and a clot is formed. This position is measured in terms of the magnitude of the wave vector $|q|=4\pi \sin \theta \lambda'$", where $\theta$ is the scattering angle and $\lambda'$ is the wavelength of the laser as modified by the index of refraction of the blood plasma. The position of the scattering peak initially moves outward as coagulation begins, and at the moment that clot formation begins the diffraction ring contracts.

FIG. 4 shows these calculations for a variety of blood samples. Azimuthal averages of each CCD image shows the diffraction ring moves inward (i.e. angular position decreases) with time for coagulating samples and remains stationary for citrated blood. The peak at the leftmost edge is the zero-order diffraction and the large dip is due to the beamblock of the direct laser beam. Samples are (a) recalcified swine blood on silicone at 37° C., and (b) citrated swine blood; samples were taken on silicone at 37° C. The initial outward movement was interpreted as a sign of the red blood cells settling in the sample. A smaller diffraction ring position indicates a larger characteristic size of the dominant scatterers. This is expected as fibrinogen molecules crosslink to form a gel network of insoluble fibrin polymers to which platelets begin to adhere as they move via diffusive forces in the sample to form a hemostatic plug. Additionally red blood cells (and other blood components) are entrapped in the fibrin network. The change in position with time of the diffraction ring follows power law behavior, i.e. position~$time^\alpha$ where the exponent $\alpha$ indicates the rate of clot formation. The position of the diffraction eventually stabilizes when the final clot state is reached, and this position indicates the strength of the final clot. The characteristic size of the aggregated cells, fibrin, and other components can be calculated again using Mie or T-matrix theory.

A second measurement can be a study of the time-dependent behavior of laser speckle patterns in the scattered light image. The dynamic laser speckle pattern is the result of light scattering from moving sample constituents. The movement of the scatterers results in phase shifts in the scattered light which result in interference patterns on the detector. The red blood cells and other blood components do not undergo motion that is purely diffusive due to the spatial constraints and various degrees of chemical and electrostatic interactions in the droplet. Depending on the imaging optics and the size of the speckles relative to the detector pixel size, either a single pixel or a select area of pixels have their intensities averaged in each frame and this averaged intensity is plotted with time. At the onset of clot formation the fibrinogen molecules are polymerized and crosslinked by thrombin. As the crosslinking reaches a critical threshold the molecules undergo a gel transition and the speckle dynamics freeze as length scale correlations diverge, leaving just the background noise. The time to this point is recorded as the time to the onset of clot formation.

An example of this measurement is shown in FIG. 5. This figure shows the averaged intensity over a 50 by 50 pixel block from a sample that contained kaolin (at a concentration of 0.2 mg of powdered kaolin to 1 mL of citrated blood). A 0.5 second smoothing filter was applied over time. The gel transition of fibrin at 201.2 seconds is evident. For this sample the speckle size was much larger than a single pixel, clearly illustrating the effect of the freezing of the speckle pattern. The point at which the speckle pattern freezes can be analytically determined in several ways, including statistical analysis of the fluctuations with time or by analyzing spectral information obtained via a Fourier transform. This measurement alone, if used on appropriate blood plasma samples, optionally with the addition of hemocompatible microspheres to provide a stronger scattering signal, is sufficient to reproduce an array of standard coagulation tests performed on blood plasma, including the thrombin time (TT), prothrombin time (PT), partial thromboplastin time (PTT), and activated partial thromboplastic time (aPTT).

A third measurement can be made by sampling a portion of the direct (i.e. unscattered) beam by averaging the pixel intensities in that region of the detector. The detected intensity is directly related to the amount of transmission through the blood sample and gives a measurement of the sample turbidity. The absorption coefficient of the blood sample can be calculated from Beer's Law. The absorption coefficient can therefore be calculated from the measured intensity. This information is directly usable in several existing blood tests, such as the prothrombin time (PT) test.

A fourth measurement that can be made by the instrument is a time-resolved autocorrelation calculation derived from series of images recorded on the detector. Photon correlation spectroscopy (also known as dynamic light scattering) uses electric field autocorrelation functions and theoretical modeling to determine the size, shape, and dynamics of microscopic scatterers in the sample. This is complementary to the Mie theory analysis and provides a different set of measurement parameters related to microscopic dynamics. In order to capture the dynamics of coagulation the time scale of the autocorrelation functions derived from pixel intensities need to be significantly shorter than the coagulation time scale. The measured time scale varies with the scattering angle, thus if using this measurement mode the imaged scattering angle must be sufficiently large to satisfy this time scale requirement. An additional detector with a separate set of imaging optics can be placed to capture higher scattering angles if desired.

One way to calculate an accurate autocorrelation curve from an image with a highly non-ergodic sample is to sample a single speckle throughout the entire time sequence. The optics can be arranged such that a single pixel corresponds to a single speckle, or a set of pixels can be sampled to represent a speckle. The autocorrelation curve is then calculated over multiple time scales (a "multi-tau" approach) and is stored. This procedure is then repeated for all pixels or set of pixels at the same scattering angle. Finally, the set of autocorrelation curves is averaged to obtain an ensemble average. Alternatively, analysis methods based on multispeckle algorithms may be used to compute autocorrelations on multiple scattering angles. This calculation can be performed either post-experiment by recording each image or as the measurement is proceeding, by analyzing and then discarding each frame. This is then repeated over the duration of the entire measurement, resulting in a final set of time-resolved autocorrelation curves. This data set can then be analyzed using predictions from models of microscopic particle and polymer physics. The data provided will complement the results from Mie scattering. This measurement technique has been used to study the formation of fibrin gels and the microrheological properties of red blood cell membranes. In one example of time-resolved autocorrelation results in fibrin gels a change was observed from stretched exponential functional behavior to power law behavior in the decay of the autocorrelation function as the sample made a transition from a sol to a gel.

FIG. 6 shows the result of autocorrelation calculations for a coagulating droplet of swine blood, illustrating time-dependent behavior. The scattering angle was too low to allow for successful resolution of the expected exponential and power law behavior. The gel network will reach a peak degree of polymerization before fibrolynisis begins to dominate and the gel network degrades, possibly to the point of a transition to sol behavior. This peak will be observed in the change in time of the power law exponent and possible reversion to stretched exponential behavior Alternative Embodiment 1

The imaging of the scattered light can be configured with a translucent screen. An imaging lens can be used to form an image of the scattered light on the screen and project it onto the detector array.

Alternative Embodiment 2

A fiber bundle can be used to capture the image of the scattered light. Here, the end of the bundle acts as the screen, with each fiber capturing a portion of the scattered light. The fibers can then be aligned with detector pixels to form the image.

Alternative Embodiment 3

An additional detector (or detector array) can be added to detect scattered light at higher scattering angles (>90°) than the forward direction if the primary detector is only imaging small scattering angles. It may be placed at any suitable angle to the laser beam. This allows for the calculation of autocorrelation functions in addition to the highly resolved small scattering angle data collected by the forward detector in any of its configurations.

Alternative Embodiment 4

An additional photodetector may be used to sample and measure the intensity of the laser beam instead of using a portion of the forward detector. A turning mirror is used to direct the unscattered laser light to a photodetector. An example (detector 24) is shown in FIG. 1.

Alternative Embodiment 5

Defocused imaging of laser speckle may be achieved to provide for high resolution measurement of autocorrelation functions and speckle intensity fluctuations. The imaging optics in any embodiment can be arranged to form a defocused image at the detector. This arrangement would preclude the measurement of static scattered light.

Alternative Embodiment 6

The scattered light image can be formed on a portion of the detector and a defocused image formed on another portion of the detector for simultaneous detection of static scattered light and laser speckle images. This may be achieved using, for example, a coaxial imaging system which forms an image of the low angle scattered light at the center of the detector, and a defocused image in an annulus around the scattered light image.

Advantages of the optical blood coagulation monitor include, without limitation, one or more of the following. The sensor has no moving parts, and can be produced in a range of sizes, from a desktop device to a handheld device. Due to its lack of moving parts the sensor can be produced in a ruggedized package. The sensor can study blood samples of any type, with or without coagulation activators or inhibitors. Blood sample sizes are small, for example <10 µl. At least four simultaneous measurement modes are available: time-resolved static scattering, optical absorption coefficient, time-resolved speckle dynamics, and time-resolved photon correlation spectroscopy. These modes provide measurements of the microscopic dynamics of coagulation and clot formations and allow for a variety of blood tests to be conducted by the instrument. Optional temperature control of the sample allows for operation in a wide range of environmental conditions. The sensor is capable of assessing the complete coagulation process to provide a similar range of information as the thromboelastograph with a higher degree of accuracy due to its higher sensitivity to coagulation dynamics. The higher sensitivity derives from the optical measurements that do not perturb coagulation. The sensor can also address a wide range of standard blood coagulation tests aside from those performed on the thromboelastograph Other embodiments will occur to those skilled in the field and are within the scope of the claims.

What is claimed is:

1. A method of determining properties of blood, comprising:
   providing a blood sample;
   providing a laser and directing light from the laser through the blood sample;
   detecting over a period of time a position of a first-order diffraction ring of laser light that is forward scattered by the blood; and
   analyzing the detected light, including the position over time of the first-order diffraction ring to provide information on time-resolved coagulation and clotting properties of the blood, wherein the provided information comprises a time for a clot to start forming, a rate of clot formation, and a strength of the clot.

2. The method of claim 1 wherein a wavelength of the laser is in the visible to near infrared range.

3. The method of claim 1 wherein the analyzing step comprises determining a time dependent statistical behavior of detected laser speckle intensities.

4. The method of claim 3 further comprising adding hemocompatible microspheres to the blood sample before directing laser light through the sample.

5. The method of claim 1 further comprising detecting an intensity of unscattered laser light that has passed through the blood sample.

6. The method of claim 5 wherein the analyzing step comprises determining a turbidity of the blood based on the detected unscattered laser light.

7. The method of claim 1 wherein the detecting step comprises sampling a single laser speckle or a plurality of speckles over time.

8. The method of claim 7 wherein the analyzing step comprises calculating an autocorrelation curve for each sampled speckle, and averaging such autocorrelations.

9. An optical blood coagulation monitor, comprising:
a blood sample holder;
a laser with its output light directed through a blood sample located in the blood sample holder;
a two-dimensional detector that detects over time a position of a first-order diffraction ring of light at a laser light wavelength, where the detector has a detector output;
optics for imaging onto the detector laser light that is forward scattered by the blood; and
a data analysis system, responsive to the detector output, that analyzes the detected light over time, including the position over time of the first order diffraction ring, to provide information on time-resolved coagulation and clotting properties of the blood, wherein the provided information comprises a time for a clot to start forming, a rate of clot formation, and a strength of the clot.

10. The optical blood coagulation monitor of claim 9 wherein a wavelength of the laser is in the visible to near infrared range.

11. The optical blood coagulation monitor of claim 9 wherein the data analysis system determines a time dependent behavior of detected laser speckle patterns.

12. The optical blood coagulation monitor of claim 11 further comprising hemocompatible microspheres that are added to the blood sample before directing laser light through the sample.

13. The optical blood coagulation monitor of claim 9 further comprising a detector for detecting an intensity of unscattered laser light that has passed through the blood sample.

14. The optical blood coagulation monitor of claim 13 wherein the data analysis system determines a turbidity of the blood based on the detected unscattered laser light.

15. The optical blood coagulation monitor of claim 9 wherein the data analysis system samples a single laser speckle or a plurality of speckles over time.

16. The optical blood coagulation monitor of claim 15 wherein the data analysis system calculates an autocorrelation curve for each sampled speckle, and averages such autocorrelations.

17. An optical blood coagulation monitor, comprising:
a blood sample holder;
a laser with its output light directed through a blood sample located in the blood sample holder, wherein a wavelength of the laser is in the visible to near infrared range;
a two-dimensional detector that detects over time a position of a first-order diffraction ring of light at a laser light wavelength, where the detector has a detector output;
optics for imaging onto the detector laser light that is forward scattered by the blood; and
a data analysis system, responsive to the detector output, that analyzes the detected light over time, including the position over time of the first order diffraction ring, to provide information on time-resolved coagulation and clotting properties of the blood, wherein the provided information comprises a time for a clot to start forming, a rate of clot formation, and a strength of the clot;
wherein the data analysis system samples a single laser speckle or a plurality of speckles over time, and determines a time dependent behavior of the time-based detected laser intensity via photon correlation spectroscopy.

* * * * *